US008388951B2

(12) United States Patent
Genkin et al.

(10) Patent No.: US 8,388,951 B2
(45) Date of Patent: Mar. 5, 2013

(54) METHOD FOR TREATING SYSTEMIC DNA MUTATION DISEASE

(75) Inventors: Dmitry Dmitrievich Genkin, Saint-Petersburg (RU); Georgy Viktorovich Tets, Saint-Petersburg (RU); Viktor Veniaminovich Tets, Saint-Petersburg (RU)

(73) Assignee: CLS Therapeutics Limited, Guernsey, Channel Islands (GB)

( * ) Notice: Subject to any disclaimer, the term of this patent is extended or adjusted under 35 U.S.C. 154(b) by 0 days.

(21) Appl. No.: 12/835,029

(22) Filed: Jul. 13, 2010

(65) Prior Publication Data

US 2010/0303796 A1   Dec. 2, 2010

Related U.S. Application Data

(63) Continuation-in-part of application No. 10/564,609, filed as application No. PCT/RU2004/000260 on Jul. 1, 2004, now abandoned.

(30) Foreign Application Priority Data

Jul. 14, 2003   (WO) .................... PCT/RU200300304
Mar. 12, 2004   (RU) ............................... 2004108057

(51) Int. Cl.
A61K 38/46 (2006.01)
C12Q 1/52 (2006.01)
C12Q 1/68 (2006.01)
C12N 9/16 (2006.01)
C07K 14/00 (2006.01)

(52) U.S. Cl. .......... 424/94.6; 435/496; 435/16; 435/6.1; 530/350

(58) Field of Classification Search .................. 435/196, 435/16, 6; 530/350; 536/23.2; 424/94.6
See application file for complete search history.

(56) References Cited

U.S. PATENT DOCUMENTS

| 5,484,589 | A | 1/1996 | Salganik |
| 5,656,589 | A | 8/1997 | Stossel et al. |
| 5,889,153 | A | 3/1999 | Suzuki et al. |
| 5,952,170 | A | 9/1999 | Stroun et al. |
| 6,033,846 | A | 3/2000 | Fournie |
| 6,156,504 | A | 12/2000 | Gocke et al. |
| 6,391,607 | B1 | 5/2002 | Lazarus et al. |
| 6,428,785 | B1 | 8/2002 | Gokeen |
| 6,455,250 | B1 | 9/2002 | Aguilera et al. |
| 6,465,177 | B1 | 10/2002 | Hoon |
| 6,521,409 | B1 | 2/2003 | Gocke et al. |
| 7,612,032 | B2 | 11/2009 | Genkin et al. |
| 2003/0044403 | A1 | 3/2003 | Shak |
| 2004/0001817 | A1 | 1/2004 | Giampapa |
| 2004/0157239 | A1 | 8/2004 | Tanuma et al. |
| 2006/0228347 | A1 | 10/2006 | Sunaga et al. |
| 2006/0233780 | A1 | 10/2006 | Genkin et al. |
| 2008/0004561 | A1 | 1/2008 | Genkin et al. |
| 2009/0053200 | A1 | 2/2009 | Genkin et al. |
| 2010/0061971 | A1 | 3/2010 | Genkin et al. |
| 2010/0150903 | A1 | 6/2010 | Genkin et al. |
| 2011/0033438 | A1 | 2/2011 | Bartoov et al. |
| 2011/0189156 | A1 | 8/2011 | Genkin et al. |

FOREIGN PATENT DOCUMENTS

| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1666055 | 2/2005 |
| EP | 1655036 | 5/2006 |
| EP | 1880733 | 1/2008 |
| EP | 2095825 | 6/2011 |
| GB | 984464 | 2/1965 |
| GB | 1005985 | 9/1965 |
| JP | 2006-290769 | 10/2006 |
| NZ | 299257 | 8/2000 |
| RU | 2099080 | 12/1997 |
| RU | 2001104426 | 1/2003 |
| RU | 2202109 | 4/2003 |
| RU | 2207876 | 7/2003 |
| RU | 2239404 | 11/2004 |
| RU | 2239442 | 11/2004 |
| RU | 2267329 | 1/2006 |
| RU | 2269356 | 2/2006 |
| RU | 2269357 | 2/2006 |
| RU | 2269359 | 2/2006 |
| RU | 2308968 | 10/2007 |
| WO | WO93/03709 | 3/1993 |

(Continued)

OTHER PUBLICATIONS

Leon et al., Cancer Research 37:646-650; 1977.*

(Continued)

*Primary Examiner* — Delia Ramirez
(74) *Attorney, Agent, or Firm* — Fish & Richardson P.C.

(57) ABSTRACT

A treatment for systemic DNA mutation diseases accompanied with development of somatic mosaicism and elevation of blood extracellular DNA and, more particularly, to a treatment of diabetes mellitus and atherosclerosis. The inventive method consist from introducing a treatment agent into a circulating blood system of a patient diagnosed with systemic DNA mutation diseases when said treatment agent destroys extracellular DNA in said blood of said patient and wherein said treatment agent used to destroy said extracellular DNA is a DNASE enzyme: said agent might be administered in doses and regimens which sufficient to decrease number average molecular weight of circulating extracellular blood DNA in the blood of said patient; such decrease of number average molecular weight might be measured by gel electrophoresis of extracellular blood DNA fraction from the blood of said patient. A DNASE enzyme may be further applied in a dose and regime that provide a DNA hydrolytic activity measured in blood plasma exceeding 1.5 Kunitz units per 1 ml of blood plasma for more than 12 hours within a period of 24 hours.

4 Claims, 2 Drawing Sheets

FOREIGN PATENT DOCUMENTS

| WO | WO95/00170 | 1/1995 |
| --- | --- | --- |
| WO | WO97/28266 | 8/1997 |
| WO | WO97/47751 | 12/1997 |
| WO | WO00/03709 | 1/2000 |
| WO | WO00/31238 | 6/2000 |
| WO | WO01/74905 | 10/2001 |
| WO | WO03/068254 | 8/2003 |
| WO | WO2005/004903 | 1/2005 |
| WO | WO2005/004904 | 1/2005 |
| WO | WO2005/007187 | 1/2005 |
| WO | WO2005/115444 | 12/2005 |
| WO | WO2006/130034 | 12/2006 |
| WO | WO2008/047364 | 4/2008 |
| WO | WO2008/066403 | 6/2008 |
| WO | WO 2011/073665 * | 6/2011 |
| WO | WO2012/075506 | 6/2012 |

OTHER PUBLICATIONS

Gormally et al., Mutation Research 635:105-117, 2007.*
Mosca et al., Clinical Rheumatology 28:1437-1440, 2009.*
Liggett et al., Journal of Neurological Sciences 290:16-21, 2010.*
Boyko et al., Journal of Neurosurgical Anesthesiology 23:222-228, 2011.*
Ye et al., Lung 188:469-474, 2010.*
Shimony et al., Acute Cardiac Care 12:109-111, 2010.*
Zaravinos et al., J. Thromb. Thrombolysis 31:180-187, 2011.*
Jylhava et al., Mechanisms of Ageing and Development 132:20-26, 2011.*
Aung et al., Hugo J 4:11-21, 2010.*
Sugihara et al., Deoxyribonuclease treatment prevents blood-borne lier metastasis of cutaneously transplanted tumour cells in mice, Br. J. Cancer (67), pp. 66-70, 1993.
Freshney, R. I., Culture of Animal Cells, A Manual of Basic Technique, Alan R. Liss, Inc., New York, pp. 3-4, 1983.
Hann, et al. Building 'validated' mouse models of human cancer. Curr Opin Cell Biol, 13(6), pp. 778-784, 2001.
Macanovic et al., The treatment of systemic lupus erythematosus (SLE) in NZB/W F1 hybrid mice; studies with recombinant murine DNase and with dexamethasone. Clinical and Experimental Immunology (106), pp. 243-252, 1996.
Zhong et al., Presence of mitochondrial tRNA(leu(UUR) A to G 3243 mutation in DNA extracted from serum and plasma of patients with type A 2 diabetes mellitus. J. Clin. Pathol. (53), pp. 466-469, 2000.
Burt et al., Detection of circulating donor deoxyribonucleic acid by microsatellite analysis in a liver transplant recipient. Liver Transpl Surg. (2), pp. 391-394, 1996.
Davis, Brian R. et al., Somatic mosaicism in the Wiskott-Aldrich syndrome: Molecular and functional characterization of genotypic revertants, Clinical Immunology, vol. 135, pp. 72-83, 2010.
Dittmar, Manuela et al., A novel mutation in the *DNASE1* gene is related with protein instability and decreased enzyme activity in thyroid autoimmunity, Journal of Autoimmunity, vol. 32, pp. 7-13, 2009.
Erickson, Robert P., Somatic gene mutation and human disease other than cancer, Mutation Research, vol. 543, pp. 125-136, 2003.
Erickson, Robert P., Somatic gene mutation and human disease other than cancer: An update, Mutation Research, vol. 705, pp. 96-106, 2010.
Gannushikina, I.V., et al., Plasma DNA Levels in Patients with Atherosclerotic Involvement of the Major Arteries of the Head and lateral Amyotrophic Sclerosis, Bulletin of Experimental Biology and Medicine, vol. 124, No. 12, pp. 1164-1166, 1997 (Translated from: Gannushkina I.V. et al., Uroven DNK v plazme krovi bolnykh s 1-4 aterosklerotischeskim porazheniem magistralnykh artery golovy i bokovym amiotroficheskim sklerozom Byulleten'Experimental' noi Biologii i Meditsiny, Moscow, Meditsina, No. 12, pp. 610-612, 1997).
Holterhus, Paul-Martin et al., Mosaicism due to a Somatic Mutation of the Androgen Receptor Gene Determines Phenotype in Androgen Insensitivity Syndrome, Journal of Clinical Endocrinology and Metabolism, vol. 82, No. 11, pp. 3584-3589 1997.
Horlitz, Martin et al., Optimized Quantification of Fragmented, Free Circulating DNA in Human Blood Plasma Using a Calibrated Duplex Real-Time PCR, PLoS ONE, vol. 4, Issue 9, e7207, 2009.
Juncosa, Barbara, DNA on the Loose: Next-Gen Blood Tests Tap Free-Floating Genetic Material, Scientific American, Mar. 18, 2009.
Kawane, K, et al., DNAse II deficiency causes chronic polyarthritis in mice, Nature Clinical Practice Rheumatology, vol. 3, No. 4, p. 192, 2007.
Malickova, Karin et al., Decreased Activity of DNase-I Predisposes to Immune-Mediated Complications in IBD Patients During Anti-TNFA Treatment, Gastroenterology, Abstract 202, vol. 138 (5 Supplement 1), S-37, 2010.
Prince, W.S., et al, Pharmacodynamics of recombinant human DNase I in serum, Clin. Exp. Immunol., vol. 113, pp. 289-296, 1998.
Ross, Kenneth Andrew, Evidence for somatic gene conversion and deletion in bipolar disorder, Crohn's disease, coronary artery disease, hypertension, rheumatoid arthritis, type-1 diabetes, and type-2 diabetes, BMC Medicine, 9:12, 2011.
Schapira, Anthony H. V., Mitochondrial disease, Lancet, vol. 368, pp. 70-82, 2006.
Shevchuk, N. A. Vremyarazreshenniy Immunofluorescentniy Analiz na DNK i Issledovanie Soderzhaniya DNK v Syvorotke Cheloveka, Voprosi Medicinskoi Khimii, No. 4, 2001 (Reference in Russian and English Translation).
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-276, 1998.
Anker, P. et al., Tumor-related alterations in circulating DNA, potential for diagnosis, prognosis and detection of minimal residual disease, Leukemia, 15, 289-91, 2001.
Ashton, G., Growing pains for biopharmaceuticals, Nature Biotech, vol. 19, pp. 307-311, 2001.
Botto, N., et al., Elevated levels of oxidative DNA damage in patients with coronary artery disease, Coronary Artery Disease, vol. 13, pp. 269-274, 2002.
Davis JC et al., Recombinant human Dnase I (rhDNase) in patients with lupus nephritis, Lupus, vol. 8, pp. 68-76, 1999.
Deitsch, et al., Transformation of malaria parasites by the spontaneous uptake and expression of DNA from human erythrocytes, Nucleic Acids Research, vol. 29, pp. 850-853, 2000.
Deocharan B. et al., Alpha-actinin is a cross-reactive renal target for pathogenic anti-DNA antibodies, J. Immunol., vol. 168, pp. 3072-3078, 2002.
Department of Health and Human Services Food and Drug Administration, Federal Register, Dec. 13, 1985, vol. 50, No. 240.
El Hassan No, et al. Rescue use of Dnase in critical lung atelectasis mucus retention in premature neonates, Pediatrics., vol. 108, pp. 468-470, 2001.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.
Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).
Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.
Gibbs et al., Mechanism-Based Target Identification and Drug Discovery in Cancer Research Science, vol. 287, pp. 1969-1973, 2000.
Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).

Gorrini, C., et al., Effect of apoptogenic stimuli on colon carcinoma cell lines with a different c-myc expression level, Int J Mol Med, vol. 11, pp. 737-742, 2003.

Gura, T., Systems for identifying New Drugs Are Often Faulty, Science, vol. 278, pp. 1041-1042, 1997.

Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.

International Search Report for PCT/RU2003/000304, mailed on Mar. 25, 2004.

International Search Report for PCT/RU2004/000260, mailed on Dec. 9, 2004.

International Search Report for PCT/RU2004/000261, mailed on Oct. 21, 2004.

International Search Report for PCT/RU2004/000262, mailed on Oct. 21, 2004.

International Search Report for PCT/RU2005/000236, mailed on Nov. 24, 2005.

International Search Report for PCT/RU2006/000642, mailed on Aug. 2, 2007.

Kalandarishvili F., Nakoplenie spontanno povrezhdennoj DNK v nei postgepatjektomirovannoj pecheni u staryh krys, Med. Novosti Gruzii, No. 5, pp. 11-12, 1998 (Reference in Russian and English-language translation).

Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.

Lachmann PJ, Lupus and Desoxyribonuclease, Lupus, vol. 12, pp. 202-206, 2003.

Lecompte, et al., Detection of free-circulating tumor-associated DNA in plasma of colorectal cancer patients and its association with prognosis, Int. J. Cancer, vol. 100, pp. 542-548, 2002.

Lee, D., Continued Marketing of a Useless Drug ('Varidase') in Panama, Lancet, Mar. vol. 335, p. 667, 1990.

Leland et al., Cancer chemotherapy—ribonucleases to the rescue, Chem. & Bio., vol. 8, pp. 405-413, 2001.

Li et al., The *Haemophilus ducreyi* cytolethal distending toxin activates sensors of DNA damage and repair complexes in proliferating and non-proliferating cells, Cellular Microbiology, vol. 4, pp. 87-99, 2002.

Maurer, HR, Bromelain: biochemistry, pharmacology and medical use, Cell Mol. Life. Sci., vol. 58, pp. 1234-1245, 2001.

Mel'Nikov D, et al., Voprosy onkologicheskoi pomoschi na etape reformirovaniya zdravookhraneniya, Ekaterinburg, pp. 159-161, 1996 (Reference in Russian and English-language translation).

Merkus et al., DNase treatment for atelectasis in infants with severe respiratory syncytial virus bronchiolitis, Eur Respir J, vol. 18, pp. 734-737, 2001.

Moreira VG et al., Usefulness of cell-free plasma DNA, procalcitonin and C-reactive protein as markers of infection in febrile patients, Annals of Clinical Biochemistry, vol. 47, pp. 253-258, 2010.

Mutirangura A., Serum/plasma viral DNA: mechanisms and diagnostic applications to nasopharyngeal an cervical carcinoma, Ann NY Acad Sci., vol. 945, pp. 59-67, 2001.

Nestle & Roberts, An extracellular nuclease from Serratia marcescens, J. Biol. Chem., vol. 244, pp. 5213-5218, 1969.

Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.

Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).

Oliven et al., Orally and Rectally Administered Streptokinase, Pharmacology, vol. 22, pp. 135-138, 1981.

Osivac et al., Reorganizacija DNK i biologicheskoje starenije, Biohimija, vol. 62, pp. 1491-1502, 1997 (Reference in Russian and English-language translation).

Perel'Man Mi, et al., Molekuljarnaja medicina i lechenie tuberkuleza, Problemi tuberkuleza, No. 5, pp. 5-7, 2001 (Reference in Russian and English-language translation).

Pisetsky, D., Immune response to DNA in systemic lupus erythematosus, Isr. Med. Assoc. J., vol. 3, pp. 850-853, 2001.

Pressler T., Review of recombinant human deoxyribonuclease (rhDNase) in the management of patients with cystic fibrosis, Biologics: Targets & Therapy, vol. 2, pp. 611-617, 2008.

Pulmozyme® (dornase alfa) Inhalation Solution product leaflet, Genetech, Inc., 2005.

Rao KS and Shrivastaw KP, Studies on the synthesis and degradation of DNA in developing and old chick cerebellum, Journal of Neurochemistry, vol. 27, pp. 1205-1210, 1976.

Raz E. et al., Anti-DNA antibodies bind directly to renal antigens and induce kidney dysfunction in the isolated perfused rat kidney, J Immunol., vol. 142, pp. 3076-3082, 1989.

Shak et al., Recombinant human DNAse I reduces the viscosity of cystic fibrosis sputum, Proc. Natl. Acad. Sci. USA, vol. 87, pp. 9188-9192, 1990.

Sherry et al., Presence and Significance of Desoxyribose Nucleoprotein in the Purulent Pleural Exudates of Patients, Proc, Soc. Exp. Biol. Med., pp. 179-184, 1948.

Simpson G., et al., Successful treatment of empyema thoracis with human recombinant deoxyribonuclease, Thorax, vol. 58, pp. 365-366, 2003.

Supplementary European Search Report for European Patent Appl. No. EP06843990, dated Nov. 23, 2009 and cf Form 1507.

Supplementary European Search Report for European Patent Appl. No. EP04748955, mailed May 19, 2009.

Supplementary European Search Report for European Patent Appl. No. EP04775224, mailed Oct. 28, 2009.

Supplementary European Search Report for European Patent Appl. No. EP05745412, dated Jul. 10, 2009.

Supplementary European Search Report for European Patent Appl. No. EP03796243, dated Jan. 12, 2010.

Tetz VV and Tetz GV, Effect of Extracellular DNA Destruction by DNase I on Characteristics of Forming Biofilms, DNA and Cell Biology, vol. 29, pp. 399-405, 2010.

Tetz, GV, et al., Effect of DNase and Antibiotics on Biofilm Characteristics, Antimicrobial Agents and Chemotherapy, vol. 53, pp. 1204-1209, 2009.

Tetz, Gv, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.

Translation of International Preliminary Report on Patentability for PCT/RU2003/000304, dated Nov. 1, 2005.

Translation of International Preliminary Report on Patentability for PCT/RU2004/000260, mailed Jan. 14, 2006.

Translation of International Preliminary Report on Patentability for PCT/RU2004/000261, mailed Dec. 2, 2005.

Translation of International Preliminary Report on Patentability for PCT/RU2004/000262, mailed Apr. 12, 2006.

Translation of International Preliminary Report on Patentability for PCT/RU2005/000236, mailed Feb. 13, 2008.

Translation of International Preliminary Report on Patentability for PCT/RU2006/000642, dated Jul. 7, 2009.

Ulrich & Friend, Toxicogenomics and drug discovery: will new technologies help us produce better drugs? Nature, vol. 1, pp. 84-88, 2002.

Varidase product information from EPGOnline, accessed on Dec. 12, 2011.

Vonmoos, P.L. and Straub, P.W., Absorption and hematologic effect of streptokinase-streptodornase (varidase) after intracavital or oral administration, Schweiz Med Wochenschr, vol. 109, pp. 1538-1544, 1979, Abstract.

Whitchurch, et al., Extracellular DNA Required for Bacterial Biofilm Formation, Science, vol. 295, p. 1487, 2002.

Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).

Zaman, et al., Direct amplification of Entamoeba histolytica DNA from amoebic liver abscess pus using polymerase chain reaction, Parasitol. Res., vol. 86, pp. 724-728, 2000.

\* cited by examiner

METHOD FOR TREATING SYSTEMIC DNA MUTATION DISEASE

CROSS-REFERENCE TO RELATED APPLICATION

This application is a Continuation-in-Part of U.S. application Ser. No. 10/564,609 filed Jan. 12, 2006 now abandoned, which is a U.S. national phase application under 35 U.S.C. §371 of International Patent Application No. PCT/RU2004/000260, filed Jul. 1, 2004 (published in Russian on Jan. 20, 2005 as WO 2005/004789), which claims priority of Russian Federation Patent Application No. RU2004108057, filed Mar. 12, 2004 and International Patent Application No. PCT/RU2003/000304 filed Jul. 14, 2003, all of which are incorporated by reference as if fully rewritten herein.

BACKGROUND OF THE INVENTION

1. Field of the Invention

The present invention relates generally to medical treatment of the systemic DNA mutation diseases accompanied with development of somatic mosaicism and elevation of blood extracellular DNA and, more particularly, to a treatment of diabetes mellitus and atherosclerosis.

2. Description of the Related Art

Mosaicism refers to a mixture of cells of different genetic composition in one individual. When DNA mutation is detectable in number, but not all somatic cells in one individual, it is called somatic mosaicism. Development of somatic mosaicism has been recently recognized as important mechanism of systemic DNA mutation diseases progression (Gottlieb B et al., Selection and mutation in the "new" genetics: an emerging hypothesis, Hum Genet. 2010 March; 127 (5): 491-501.) Importance of somatic mosaicism involving disease-causing mutations has been reported for variety of monogenic (reviewed by Youssoufian H., Nature Reviews Genetics 3, 748-758, October 2002) and more recently for multifactor DNA mutation diseases: cardiac rhythm disorders (M. H. Gollob et al., Somatic mutations in the connexin 40 gene (GJA5) in atrial fibrillation, N. Eng. J. Med. 354 (2006), pp. 2677-2688.); atherosclerosis (S. De Flora et al., Mutagenesis and cardiovascular diseases. Molecular mechanisms, risk factors, and protective factors, Mutat. Res. 621 (2007), pp. 5-17), systemic vascular disorders (B. Gottlieb et al., BAK1 gene variation and abdominal aortic aneurysms, Hum. Mutat. 30 (2009), pp. 1043-1047); immune deficiencies (Wada T. et al., Somatic mosaicism in primary immune deficiencies, Curr Opin Allergy Clin Immunol. 2008 December; 8(6): 510-4); Alzheimer disease (Beck J A et al., Somatic and germline mosaicism in sporadic early-onset Alzheimer's disease. Hum Mol Genet. 2004 Jun. 15; 13(12): 1219-24.); diabetes mellitus (Emma L. Edghill et al, Origin of de novo KCNJ11 mutations and risk of neonatal diabetes for subsequent siblings. The Journal of Clinical Endocrinology & Metabolism Vol. 92, No. 5 1773-1777).

According to current knowledge the systemic DNA mutation diseases represent very distinct subsets of human pathology different in etiology and pathogenesis and accordingly has fundamentally different, usually palliative treatment modalities—cholesterol lowering therapy for atherosclerosis (New Concepts and Paradigms in Cardiovascular Medicine: The Noninvasive Management of Coronary Artery Disease, K. Lance Gould, THE AMERICAN JOURNAL OF MEDICINE, Volume 104, Jun. 22, 1998, pp. 2-17) and insulin therapy or insulin sensitization therapy for diabetes mellitus (Pharmacological Management of Diabetes: Recent Progress and Future Perspective in Daily Drug Treatment, Gerard Emilien et al., Pharmacol. Ther. Vol. 81, No. 1, pp. 37-51, 1999).

More recently the gene therapy was recognized as potential tool for disease specific intervention which may target the function of certain specific disease involved genes and provide more efficient cure based on repair of existing genetic defects in atherosclerosis (Ishisaki A, et al., Novel ideas of gene therapy for atherosclerosis: modulation of cellular signal transduction of TGF-beta family. Curr Pharm Des. 2006; 12(7): 877-86; Harris J D, et al. ApoE gene therapy to treat hyperlipidemia and atherosclerosis. Curr Opin Mol Ther. 2006 August; 8(4): 275-87; Hayden et al. Gene therapy method for reducing risk of atherosclerosis, U.S. Pat. No. 6,784,162) and diabetes mellitus (G B Parsons, Ectopic expression of glucagon-like peptide 1 for gene therapy of type II diabetes, Gene Therapy (2007) 14, 38-48; L. Chan, In vivo gene therapy for diabetes mellitus, Trends in Molecular Medicine, Volume 9, Issue 10, October 2003, Pages 430-435; M. During, Compositions for gene therapy of diabetes, EP1889914).

However no cure exists which may target the evolution of disease causing DNA mutations leading to development of somatic mosaicism. Accordingly, the development of new effective, non-toxic method that may suppress the development of somatic mosaicism and consequently be effective cure for systemic DNA mutation disease is an extremely important task.

Circulating extracellular nucleic acids were discovered more than 60 years ago (Anker P Circulating DNA in plasma or serum, Clin Chim Acta. 2001 November; 313(1-2): 143-6). However until now elevated levels of extracellular blood DNA in systemic DNA mutation diseases, and in particular in atherosclerosis and diabetes mellitus were considered only as useful diagnostic and research tool (El Tarhouny S. A. et al., Assessment of cell-free DNA with microvascular complication of type II diabetes mellitus, using PCR and ELISA. Nucleosides Nucleotides Nucleic Acids. 2010 March; 29(3): 228-36; Langford M P et al., Plasma levels of cell-free apoptotic DNA ladders and gamma-glutamyltranspeptidase (GGT) in diabetic children. Exp Biol Med (Maywood). 2007 October; 232(9): 1160-9; Arnalich F. et al., Prognostic value of cell-free plasma DNA in patients with cardiac arrest outside the hospital: an observational cohort study, *Critical Care* 2010, 14; Arnalich F. Association of cell-free plasma DNA with preoperative mortality in patients with suspected acute mesenteric ischemia, Clinica Chimica Acta, in press; Zhong S, Presence of mitochondrial tRNA (Leu (UUR)) A to G 3243 mutation in DNA extracted from serum and plasma of patients with type 2 diabetes mellitus 2000 June; 53(6): 466-9.)

Circulating extracellular nucleic acids have never been considered as potential therapeutic target in systemic DNA mutation diseases. Accordingly, no therapeutic method was developed which targets extracellular blood DNA in systemic DNA mutation diseases. Thus it makes impossible to take any technical solution as prototype.

As used in this application, the following terms are meant to have the following corresponding definitions.

Deoxyribonuclease (DNASE) is any enzyme that catalyzes the hydrolytic cleavage of phosphodiester linkages in the DNA backbone.

Extracellular blood DNA number average molecular weight—the number average molecular weight is a way of determining the molecular weight of a polymer. The number average molecular weight is the ordinary arithmetic mean or average of the molecular weights of the individual DNA macromolecules. It is determined by measuring the molecular weight of n polymer molecules, summing the weights, and dividing by n. The number average molecular weight of extracellular blood DNA can be determined by gel electrophoresis. The shift of extracellular blood DNA bands to low-MW areas reflect decrease number average molecular weight and in fact reflects enzymatic cleavage of extracellular blood DNA.

DNA mutation disease refers to diseases where specific DNA mutation has been identified as single leading cause (monogenic or single gene disorders) or multifactor disorders resulting from mutations in multiple genes, often coupled with environmental causes.

Systemic disease is one that affects a number of organs and tissues, or affects the body as a whole.

SUMMARY OF THE INVENTION

The object of this invention is to develop high-performance and low-toxic method for treatment of systemic DNA mutation diseases accompanied with development of somatic mosaicism and elevation of blood extracellular DNA and, more particularly, to a treatment of diabetes mellitus and atherosclerosis.

According to the invention this task is resolved by introducing a treatment agent into a circulating blood system of a patient diagnosed with systemic DNA mutation disease when said treatment agent destroys extracellular DNA in said blood of said patient and wherein said treatment agent used to destroy said extracellular DNA is a DNASE enzyme. In one of preferred embodiments said agent must be administered in doses and regimens which sufficient to decrease number average molecular weight of circulating extracellular blood DNA in the blood of said patient; such decrease of number average molecular weight might be measured by gel electrophoresis of extracellular blood DNA fraction from the blood of said patient. In one of preferred embodiments the method according the invention can be effectively applied for treatment of diabetes mellitus and atherosclerosis. A DNASE enzyme may be further applied in a dose and regime that results in a DNA hydrolytic activity measured in blood plasma that exceeding 1.5 Kunitz units per 1 ml of blood plasma for more than 12 hours within a period of 24 hours.

The present invention suggests that systemic DNA mutation disease can be treated by reducing of circulating extracellular blood DNA levels.

Development of systemic DNA mutation disease in humans is accompanied by quantitative and/or qualitative change of blood extracellular DNA.

There are no analysis of blood extracellular DNA spectrum and its biological role in systemic DNA mutation disease prior to this invention. A search of the prior art reveals no published data concerning an analysis of blood extracellular DNA spectrum in systemic DNA mutation disease performed by direct cloning and without use of polymerase chain reaction (PCR). PCR can pervert a pattern of blood extracellular DNA because of specificity of primers used for amplification. There is no available knowledge about genetic repertoire of extracellular blood DNA in patients suffering from systemic DNA mutation disease and about biological role of extracellular blood DNA in course of these diseases. Nothing is known about potential therapeutic value of extracellular blood DNA enzymatic destruction for treatment of systemic DNA mutation disease; so, taking into account all aforesaid, the invention complies with requirements of "novelty" criteria (N).

As the applicant established by direct cloning and sequencing of extracellular blood DNA without PCR (Polymerase Chain Reaction), the extracellular blood DNA of patients with systemic DNA mutation disease contains the unique quantitative and qualitative repertoire of genes, which non-randomly represents human genome and contains genetic elements involved in to the development of the disease. It was shown that extracellular blood DNA might promote the development of somatic mosaicism and systemic DNA mutation disease.

It was established that enzymatic destruction of extracellular blood DNA by DNASE enzyme when applied in certain surprisingly high specific doses has significant therapeutic effect on the course of systemic DNA mutation disease.

Aforesaid new characteristics of the claimed invention are based on new ideas about mechanism of development of systemic DNA mutation disease. In this way the claimed method conformances to requirements of "invention step" criteria (IS).

BRIEF DESCRIPTION OF THE DRAWINGS

The advantages and features of the present invention have been explained by detailed description of embodiments with references to drawings.

DESCRIPTION OF THE PREFERRED EMBODIMENTS

Figure 1:
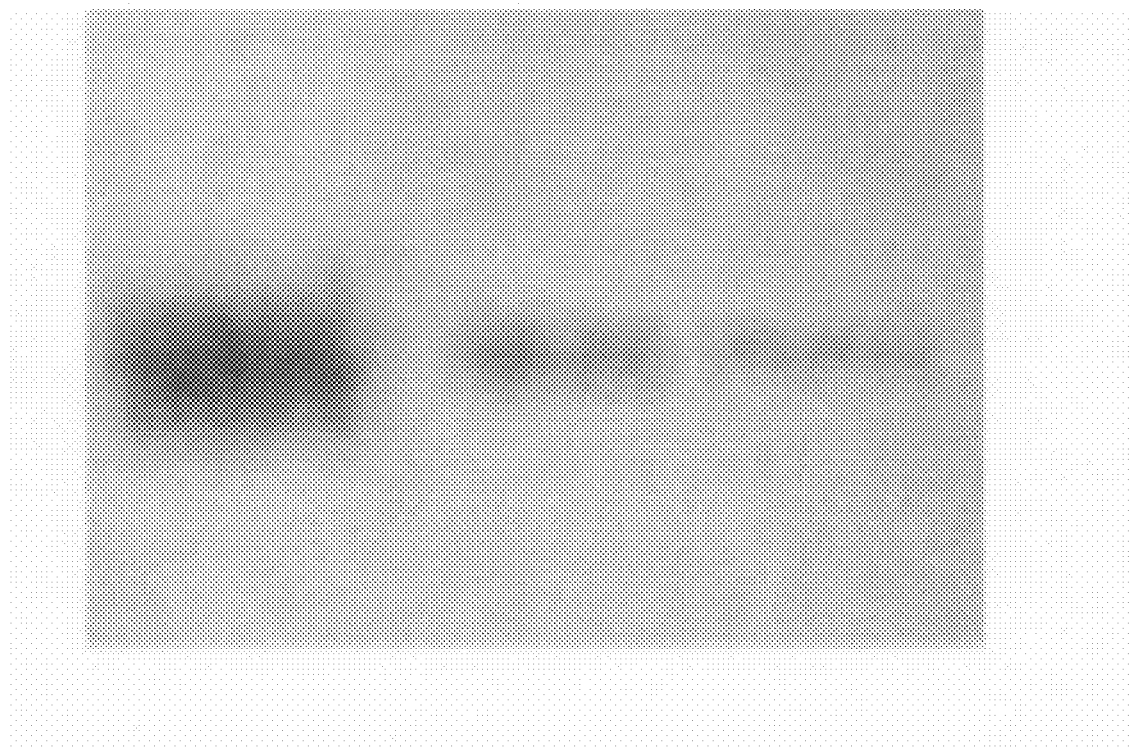
FIG. 1: Extracellular blood DNA fraction from patient suffering from systemic atherosclerosis increases the expression of NF-kappa B protein in cultured aortic endothelial cells (A); treatment of extracellular blood DNA with DNASE enzyme ameliorates this effect (B)

The inventive method is realized as follows:
Materials and Methods:
The following agents, which destroy extracellular blood DNA, were used: bovine pancreatic DNASE (Sigma, specific activity 2 400 Kunitz units/mg; Samson-Med, specific activity 1 500 Kunitz units/mg), recombinant human DNASE 1 (Gentech, specific activity 1000 U/mg).

Extracellular DNA from blood plasma was isolated as follows: fresh plasma (no more than 3-4 hours after sampling) with anticoagulant (sodium citrate) was centrifuged on Ficoll-Plaque Plus (Amersham-Pharmacia) during 20 minutes at 1500 g. at room temperature. ½ of plasma was detached, not affecting the rest of cells on the Ficoll pillow, and further centrifuged at 10000 g. during 30 min for separation from cell fragments and debris. Supernatant was detached, without affecting of the sediment, and was toped up to 1% of sarkosil, 50 mM tris-HCl, pH 7.6, 20 mM EDTA, 400 mM NaCl, and than mixed with equal volume of phenol-chloroform (1:1) mixture. The prepared emulsion was incubated during 2 hours at t=65° C., then phenol-chloroform mixture was separated by centrifuging (500 g during 20 minutes, room temperature). The procedure of deproteinization with phenol-chlorophorm mixture was repeated 3 times, and then the water phase was processed with chloroform and diethyl ether. Separation from organic solvents was made by centrifugation at 5000 g during 15 minutes. Then equal volume of izopropanol was added to resulting aqueous phase and the mixture was incubated overnight at 0° C. After sedimentation the nucleic acids were separated by centrifugation at 10000 g during 30 minutes. The sediment of nucleic acids was dissolved in of 10 mM tris-HCl buffer, pH 7, 6 with 5 mM EDTA, and inflicted to the CsCl gradient (1M, 2.5M, 5.7M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (t=4° C.) and pooled. Presence of DNA in fractions was determined by agar electrophoresis and DNA was visualized by ethidium bromide staining. The amount of DNA was determined with spectrophotometer (Beckman DU70) in cuvetts (100 mkl) at wavelength of 220-230 nm.

NOD mice were obtained from <<Pushcino>> animal breeding house.

Example 1

DNASE Treatment Suppresses the Development of Somatic Mosaicism

Frequency of HPRT gene's mutations in blood T-lymphocytes was studied as the model of development of somatic mosaicism in vivo. The human HPRT gene, mapped to chromosome Xq26, codes for a constitutively expressed, but non-essential, enzyme involved in purine metabolism. Mutant peripheral blood T-lymphocytes which do not express a functional HPRT gene product can be enumerated and clonally expanded by selective growth in the normally toxic purine analog 6-thioguanine in the presence of specific mitogens and growth factors. In normal, unexposed individuals the frequency of 6-thioguanine resistant T-lymphocytes is typically $10^{-6}$ to $10^{-5}$ (R. J. Albertini, J. A. Nicklas, J. P. O'Neill, S. H. Robison, In vivo somatic mutations in humans: measurement and analy-sis, Annu. Rev. Genet. 24 Ž1990. 305-326.) Molecular analyses of the mutant, HPRT deficient, clones have demonstrated that 85% of the gene inactivating mutations observed in unexposed adults arises by localized HPRT gene alterations—single base changes, small deletions or insertions and frame shift Selective lymphocyte cloning was performed using peripheral blood of 8 female patients with different forms of advanced cancer who got surgical resection at Kostushko municipal Hospital (St. Petersburg) and immunomodulation therapy at neoadjuvant setting (Neovir, 250 mg IM once every 2 days for 3 weeks). Following surgical resection 4 patients were further treated by IV infusions of bovine pancreatic DNASE (Samson) according the following schedule: 2000 mkg/kg×4 times daily for 21 day. Following completion of treatment the patients were assayed for HPRT (−) mutation in blood lymphocytes.

Mononuclear cells were isolated from the whole blood samples using Ficoll-Paquee (Becton Dickinson). Mitogenic stimulation of the separated lymphocytes ($1\times10^6$/ml) was initiated with 1 mg/ml phytohemagglutinin (PHA) in RPMI 1640 media supplemented with penicillin (100 U/ml), streptomycin (100 mg/ml), 20% nutrient medium HL-1 and 5% BSA at 5% CO2 at 37° C. for 24 h. Following wash the cells were then seeded in 96-well round-bottomed plates at cell density of $2\times10^4$ cells per well in selection medium to determine cloning efficiency. The cells were plated in 200 ml of the RPMI medium containing 1 mg/ml 6-thioguanine, 0.125 mg/ml PHA, 20% HL-1 and 5% BSA supplemented with interleukin-2 (BD Biosciences, 10 BRMP units/mi). Four 96-well plates were seeded for each patient. After 5 days of culture, the colonies on mutant selection plates were scored for growth using an inverted microscope. The results of selective T-lymphocyte cloning are presented in the table below:

| Patient | Treatment | Total number of wells | HPRT⁻ wells (growth positive) |
|---------|-----------|----------------------|-------------------------------|
| K N P   | DNASE     | 384                  | 7                             |
| P G P   | DNASE     | 384                  | 12                            |
| B A I   | DNASE     | 384                  | 2                             |
| F V V   | DNASE     | 384                  | 11                            |
| S L S   | NO        | 384                  | 47                            |
| G A N   | NO        | 384                  | 22                            |
| P M I   | NO        | 384                  | 31                            |
| E N V   | NO        | 384                  | 55                            |

Thus, inventive treatment suppresses spread of HPRT (−) mutation and suppresses the development of somatic mosaicism.

Example 2

Extracellular Blood DNA Promotes the Development of Somatic Mosaicism

The extracellular blood plasma DNA was purified from blood of patient ENV as specified in methods section. Mononuclear cells were isolated from the whole blood samples of patients KNP, PGP, BAI and FVV as specified in Example 1. The mitogenic stimulation and selective cloning were performed as specified in Example 1 with modification as follows: during mitogenic activation stage lymphocyte cultures of patients KNP, PGP, BAI and FVV were supplemented with 50 mkg/ml of extracellular blood plasma DNA purified from patient ENV. After 5 days of culture, the colonies on mutant selection plates were scored for growth using an inverted microscope. The results of selective T-lymphocyte cloning are presented in the table below:

| Patient | Total number of wells | HPRT⁻ wells (growth positive) |
|---------|----------------------|-------------------------------|
| K N P   | 384                  | 18                            |
| P G P   | 384                  | 15                            |
| B A I   | 384                  | 21                            |
| F V V   | 384                  | 31                            |

Thus, extracellular blood DNA promotes the development of somatic mosaicism.

Example 3

Sequencing of Extracellular Blood DNA from the Patient Suffering from Type 2 Diabetes and Systemic Atherosclerosis. Treatment of Atherosclerosis A 54-years-old man has been admitted to the Cardiothoracic surgery department of Kostushko municipal hospital (St. Petersburg) in severe condition complaining on intensive pain in abdomen, diarrhea, intensive pain in legs that appear during walking, loss of weight. Diabetes mellitus type 2 was diagnosed 12 years ago and glybencamide was prescribed. Pain in epigastrium after food intake appeared 15 months ago. Antacids were prescribed but pain continued to increase and steatorrhea appeared in the last 3 months. Because of intensive pain syndrome anorexia has developed in a couple of days prior admittance. Considerable exhaustion (body weight was 44 kg; body weight loss was 28 kg for the last 5 months) and absence of arterial pulsation on legs were found out during examination. No organic changes were observed during gastroduodenoscopy and colonoscopy. Electrocardiographic data was not changed pathologically. Moderate increase of cholesterol level and low-density lipoprotein fraction was observed in blood analysis. Glycated hemoglobin' level was 11%. Partial occlusion of aorta below renal artery (70%), partial occlusion of iliac arteries (90%), total occlusion of upper and lower mesenteric artery were observed on aortography.

The probes of patient's extracellular blood DNA were taken before initiation and on day 35 of therapy. The extracellular DNA was cloned by the method which allows to get non amplified plasmid libraries of blood extracellular DNA with representativeness up to one million of clones with the average size of 300-500 base pairs. The DNA which has been isolated using the protocol specified in Materials and Methods section was treated with Proteinase K (Sigma) at 65° C. and subjected to additional phenol-chloroform extraction step with further overnight precipitation by ethanol. The DNA fraction was than treated by Eco RI restrictase or by Pfu polymerase (Stratagene) in presence of 300 mkM of all desoxynucleotidetriphosphates for sticky-ends elimination. The completed DNA was phosphorylated by polynucleotidkinase T4 and ligated to pBluescript plasmid (Stratagene), which had been digested with EcoRI or PvuII and dephosphorylated by phosphatase CIP (Fermentas). The process of ligation was conducted with Rapid Legation Kit (Roche). The ligated library was transformed into DH12S cells (Life Technologies) by electroporation (*E. Coli* porator; BioRad). 12-20 electroporation covets were used for the transformation of one library. The library serial dilutions were cloned on 1.5% agar and LB media supplemented with ampicillin. In both cases the libraries represented 2-3×10$^6$ clones.

Analysis of 75 randomly selected clones with the size 300-1000 base pairs from the "before treatment" library revealed 56 clones containing unique human DNA sequences as presented at the table below:

| Gene | Number of clones | Potential role in atherosclerosis/diabetes mellitus |
| --- | --- | --- |
| Neutral endopeptidase | 2 | At atherosclerosis its activity is increased in endothelial cells, nonstriated muscle cells, stromal cells of artery' intima. Decreasing of its activity can decrease lipids accumulation in vessels wall. |
| Muskelin 1 | 1 | Works as mediator of cell response on thrombospondin 1. Thrombospondin 1 - mediated processes are pathophysiological components of atherosclerotic affection of artery wall. |
| Nf-kappaB | 3 | At hyperglycemia and atherosclerosis activity is increased in cells of artery wall. |
| E-selectin | 3 | High level of expression is a risk factor of angiopathy development at diabetes type 2. |
| GAD2: glutamate decarboxylase 2 | 2 | One of the main pancreatic autoantigens |
| Phospholipase C, epsilon | 2 | Induces expression of receptors of low-density lipoproteins. |
| BAI3: brain-specific angiogenesis inhibitor | 1 | Angiogenesis inhibitor |
| Nicotinamide nucleotide transhydrogenase | 1 | Involved in detoxification of reactive oxygen species and insulin secretion. |
| 17 kD fetal brain protein | 1 | UNCLEAR |
| CRTL1: cartilage linking protein 1 | 1 | Involved in morphogenetic process in heart and large vessels |
| Transient receptor potential cation channel | 1 | UNCLEAR |

Thus, extracellular blood DNA from patient having diabetes mellitus and systemic atherosclerosis contains significant non-random presence of human disease-relevant unique genomic DNA.

Patient was considered as not eligible for surgery so, conservative therapy was chosen. Intensive IV nutrition was started. Insulin and anti-aggregation therapy have being started. Under patient consent daily intravenous infusions of bovine pancreatic DNASE (Samson) at daily dose of 800 mg (1 200 000 Kuntz units) divided to 4 two-hour deliveries were started. Week after start of DNASE therapy pain syndrome disappeared and patient was allowed to take light dietetic food orally. 20 days after start of DNASE treatment patient was switched to full value oral nutrition. General state was improved, body weight has increased. 45 days following initiation of DNASE treatment patient was reexamined by angiography. 20% decrease of aorta occlusion and 35% decrease of iliac artery occlusion level as well as appearance of blood circulation in upper and lower mesenteric was observed. Patient was considered as eligible for revascularization surgery.

Extracellular blood plasma DNA sampled from patients blood at day 35 following start of DNASE therapy was assayed by gel electrophoresis and cloning. Analysis of 50 clones randomly chosen from the library obtained from the extracellular blood plasma DNA of patient on the day 35 after the beginning of treatment has shown that more than 90% of revealed clone sequences are short fragments of repetitive human DNA with the dominance of alpha-satellite DNA.

Example 4

Influence of Extracellular Blood DNA from the Patient with Systemic Atherosclerosis on Disease Causing Protein Expression in Aortic Endothelial Cells Endothelial NF-kappa B signaling orchestrates proinflammatory gene expression at the arterial wall and promotes the pathogenesis of atherosclerosis. Here we assayed the influence of extracellular blood DNA from the patient diagnosed with systemic atherosclerosis on NF kappa B expression in primary aorta endothelial cell culture. Blood plasma was obtained from vascular surgery clinic of St. Petersburg Medical Academy from the patient undergoing femoro-femoral bypass surgery due to severe atherosclerotic arterial occlusion.

The extracellular blood DNA was purified as described in Materials and Methods section. The aortic endothelial cells (C-006-5C; Invitogen) were plated at density of 5-8×10² cells/mm² in multiwell (12×) cell culture plates in Clonetics® EGM®-2MV media (Lonza Cologne AG) and incubated for 48 h. at 37° C. and 5% $CO_2$. Following 24 h of growth the culture media was supplemented with 50 mkg/ml of patient extracellular blood DNA fraction or 50 mkg/ml of patient extracellular blood DNA fraction plus human recombinant DNASE-1 (Genentech) at 1 mkg/ml concentration.

After 24 h. culturing the explants were lysed in buffer containing 20 mM Tris-HCl, 150 mM NaCl, 1 mM phenylmethylsulfonylfluoride, 5 mg/ml aprotinin, 0.5% Nonidet P-40 (Sigma-Aldrich) for 1 hour at 4° C. The lysates were centrifuged for 10 min at 20,000 rpm. The supernatants were diluted with reducing sample buffer and were separated by electrophoresis on a 10% SDS-PAGE gel (20 mkg protein per lane loaded). The proteins were transferred onto Hybond-C-nitrocellulose membrane (Amersham Italia, Milan, Italy. For immunoblot analysis, the membranes were incubated with the NF-κB antibodies (Stressgen). The bands were detected using the chemiluminescence system.

The results are presented at the FIG. 1. Extracellular blood DNA fraction from patient suffering from systemic atherosclerosis increases the expression of NF-kappa B in cultured aortic endothelial cells and treatment with DNASE ameliorate this effect.

Example 5

Treatment of Diabetes Mellitus

Figure 2A:
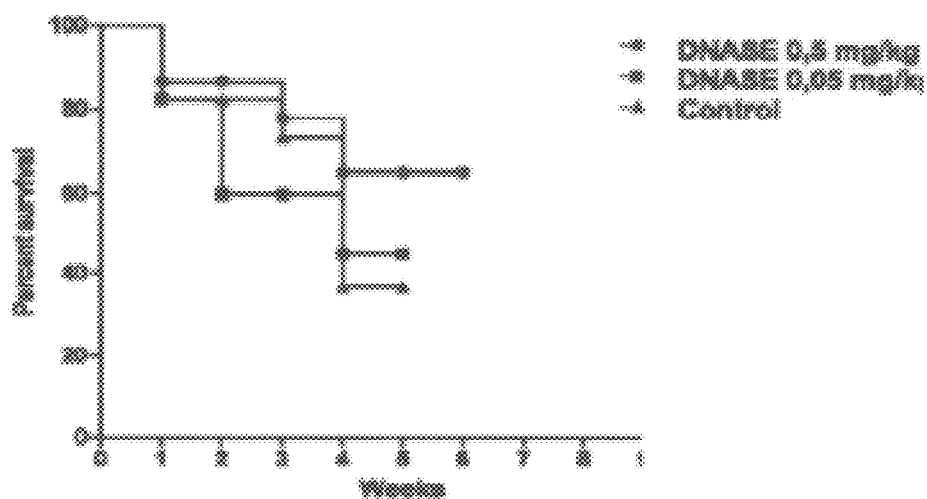
FIG. 2: A: Increased survival of NOD diabetic mice treated with different doses of DNASE 1-evident increase in survival of mice treated with 500 mkg/kg DNASE 1; B: evident decrease of average molecular weight of extracellular blood plasma DNA (as measured by electrophoresis) in blood of NOD diabetic mice treated with 500 mkg/kg DNASE 1.
Figure 2B:
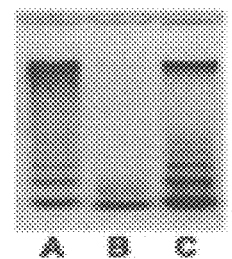

Non-obese diabetic (NOD) mice exhibit a susceptibility to spontaneous development of autoimmune insulin dependent diabetes mellitus. 60 NOD mice were recruited to the study at the age of 14 weeks when all of them became hyperglycemic. The recombinant human DNASE 1 (Gentech) at 50 mkg/kg and 500 mkg/kg was administered intramuscularly twice daily for 21 day. 2 mice from each group were sacrificed at the last treatment day to perform evaluation of extracellular blood plasma DNA. The efficacies of DNASE were assessed based on the survival rate at day 35. The results of experiments are presented at the FIG. 2. There is evident increase in survival of mice treated with 500 mkg/kg DNASE 1; such survival is accompanied with decrease of average molecular weight of extracellular blood plasma DNA (as measured by electrophoresis) in blood of NOD diabetic mice. Thus, high doses of DNASE according to inventive treatment are able to decrease the quantities of circulating extracellular blood plasma DNA and are effective against systemic DNA mutation disease-diabetes mellitus.

Example 6

Treatment of Diabetes Mellitus

A 46-years-old patient with 3 years history of type 2 diabetes mellitus was admitted to the internal therapy clinic of St. Petersburg Medical Academy. Patient failed to achieve proper glucose control using oral hypoglycemic agents including those of thiazolidinediones, biguanides and sulfonylureas. Patient was switched to 0.3 IU/kg of NPH insulin monotherapy (21 IU daily) and discharged from clinics under the supervision of ambulatory endocrinologist. Three month later patient was readmitted to the clinic since glycosylated hemoglobin (HbA1) level was still too high (above 10%) with evolving microalbuminuria and decrease in vision sharpness despite daily insulin dose was adjusted up to 1.2 U/kg (84 U/day) during ambulatory period. Under patient consent he was assigned for intramuscular injections of bovine pancreatic DNASE (Samson) twice daily at 200 mg/day dose for 4 months and again discharged from clinics. At 4 month after initiation of treatment patient were reexamined in clinics outpatient department. Significant improvement in insulin sensitivity, improvement of glycemia control and normalization of kidney function has been reported by patient ambulatory endocrinologist and confirmed by laboratory examination in clinic. The effect of DNASE treatment on patient disease indicators is presented in table below:

| Indicator | Prior DNASE treatment | At DNASE course completion |
|---|---|---|
| Insulin requirement | 1.2 IU/kg | 0.6 IU/kg |
| HbA1 | 13.2% | 7.2% |
| 24 h. albuminuria | 275 mg | 60 mg |

Thus, the inventive treatment is effective in diabetes mellitus.

INDUSTRIAL APPLICABILITY

For the realization the methods there were used well-known materials and equipment manufactured in plant conditions and according to aforesaid the invention conformances to requirements of "industrial applicability" criteria (IA)

What is claimed is:

1. A method for treating diabetes mellitus in a patient in need thereof, wherein said method comprises introducing a DNase enzyme into the blood circulation of said patient, wherein said DNase enzyme is administered in a dose and regimen which is sufficient to decrease the average molecular weight of extracellular blood DNA in the blood of said patient as measured by gel electrophoresis of extracellular blood DNA fraction from the blood of said patient.

2. A method for treating atherosclerosis in a patient in need thereof, wherein said method comprises introducing a DNase enzyme into the blood circulation of said patient, wherein said DNase enzyme is administered in a dose and regimen which is sufficient to decrease the average molecular weight of extracellular blood DNA in the blood of said patient as measured by gel electrophoresis of extracellular blood DNA fraction from the blood of said patient.

3. The method according to claim 1, wherein said DNase enzyme is administered in a dose and regimen that results in a DNA hydrolytic activity measured in blood plasma that exceeds 1.5 Kunitz units per 1 ml of blood plasma for more than 12 hours within a period of 24 hours.

4. The method according to claim 2, wherein said DNase enzyme is administered in a dose and regimen that results in a DNA hydrolytic activity measured in blood plasma that exceeds 1.5 Kunitz units per 1 ml of blood plasma for more than 12 hours within a period of 24 hours.

* * * * *